US012747197B2

(12) United States Patent
(10) Patent No.: US 12,747,197 B2
(45) Date of Patent: Sep. 29, 2026

Park et al.

(54) METHOD FOR PREPARING MODIFIED NATURAL OIL USING ORGANOCATALYST SUPPORTED ON POLYMER AND MODIFIED NATURAL OIL PREPARED USING THE SAME

(71) Applicant: KOREA RESEARCH INSTITUTE OF CHEMICAL TECHNOLOGY, Daejeon (KR)

(72) Inventors: Sae-Hume Park, Daejeon (KR); Ji-Hoon Shin, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 588 days.

(21) Appl. No.: 18/205,621

(22) Filed: Jun. 5, 2023

(65) Prior Publication Data

US 2024/0002327 A1 Jan. 4, 2024

(30) Foreign Application Priority Data

Jun. 29, 2022 (KR) ........................ 10-2022-0079542

(51) Int. Cl.
*C07C 67/26* (2006.01)

(52) U.S. Cl.
CPC .................................... *C07C 67/26* (2013.01)

(58) Field of Classification Search
CPC ....... C07C 67/26; C07C 69/708; C07C 67/31; C11C 3/006; C11C 3/08; C11C 1/08; C11C 3/10
See application file for complete search history.

(56) References Cited

U.S. PATENT DOCUMENTS 8,308,975 B2 11/2012 Roh et al.
2009/0286896 A1* 11/2009 Roh .................. C08G 18/4829 528/65

FOREIGN PATENT DOCUMENTS

KR 10-2010-0056755 5/2010
KR 20100056755 A * 5/2010 ........... C07D 453/02
KR 10-2015-0087214 7/2015
KR 10-1839877 3/2018
KR 102012540 8/2019

OTHER PUBLICATIONS

Machine translation of KR-20100056755-A. (Year: 2010).*
Chaoqun Zhang et al., "Polyurethanes from Solvent-Free Vegetable Oil-Based Polyols", ACS Sustainable Chem. Eng. 2014, 2, 2465-2476, Sep. 15, 2014.
Kemal Karadeniz et al., "Ring Opening of Epoxidized Soybean Oil with Compounds Containing Two Different Functional Groups", J Am Oil Chem Soc (2015) 92:725-731, Mar. 29, 2015.

(Continued)

*Primary Examiner* — Deborah D Carr
(74) *Attorney, Agent, or Firm* — LEX IP MEISTER, PLLC

(57) ABSTRACT

Provided are a method for preparing modified natural oil using an organocatalyst supported on a polymer and a modified natural oil prepared using the same. According to the present invention, there are effects of increasing the content of monomers as a main product of modified natural oil, minimizing side products, and easily recovering and repeatedly reusing organocatalysts supported on a polymer.

9 Claims, 4 Drawing Sheets

(56) References Cited

OTHER PUBLICATIONS

Nitish Deshpande et al., "Epoxide ring opening with alcohols using heterogeneous Lewis acid catalysts: Regioselectivity and mechanism", Journal of Catalysis 370 (2019) 46-54, Dec. 20, 2018.
KIPO, Office Action of the corresponding Korean Patent Application No. 10-2022-0079542, dated Nov. 8, 2024, total 10 pages.
KIPO, Written Decision on Registration of the corresponding Korean Patent Application No. 10-2022-0079542, dated Jul. 29, 2025, total 10 pages.

* cited by examiner

[FIG. 1]
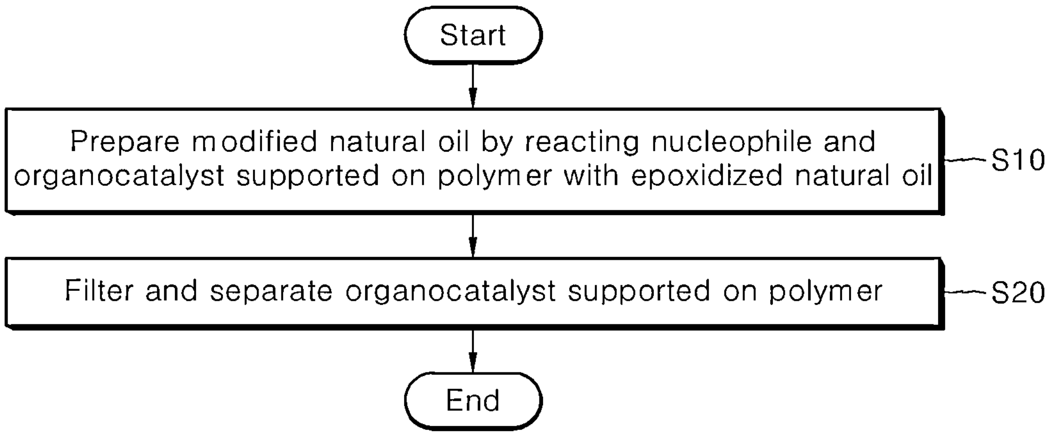

[FIG. 2]
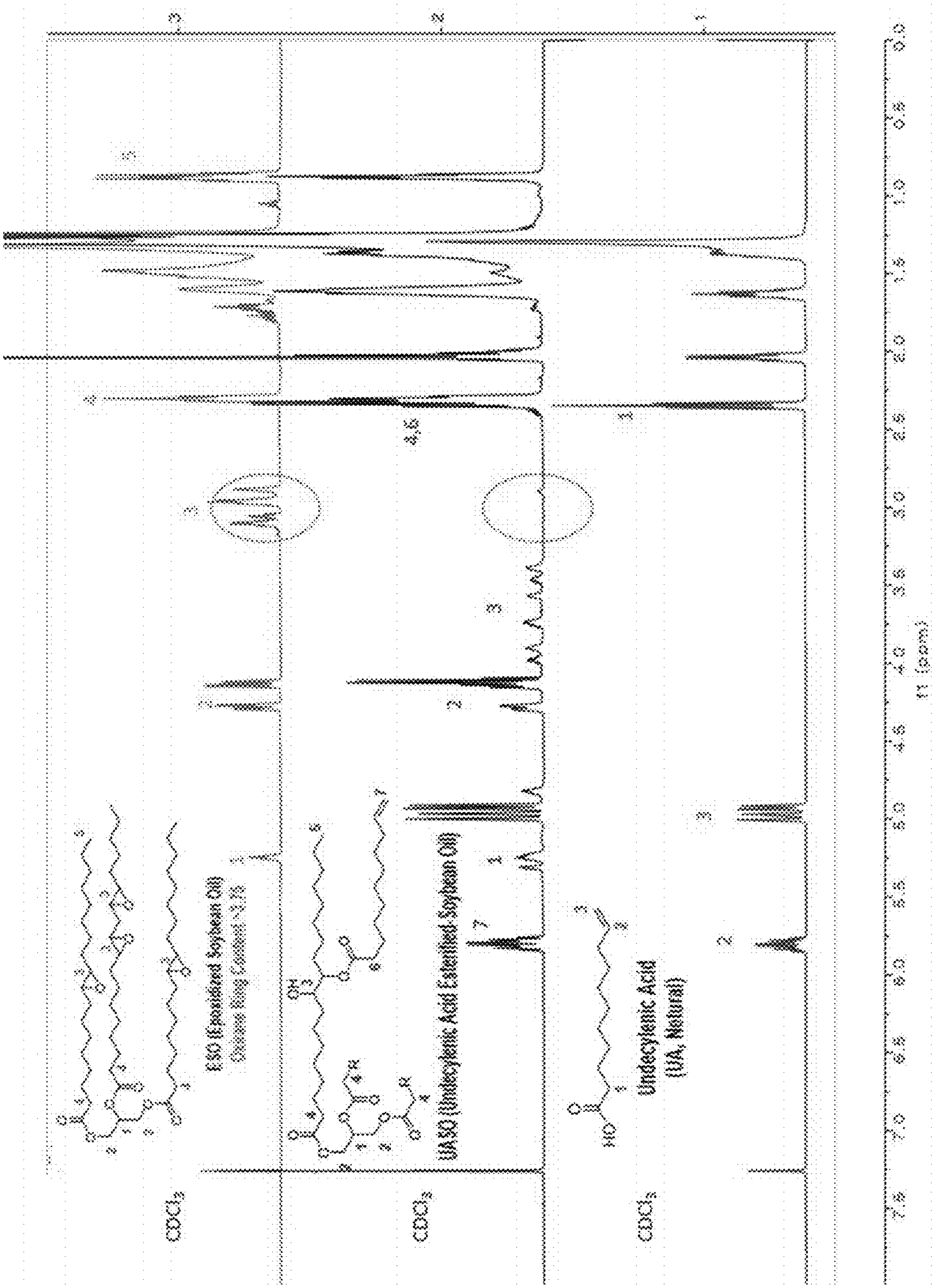

[FIG. 3]
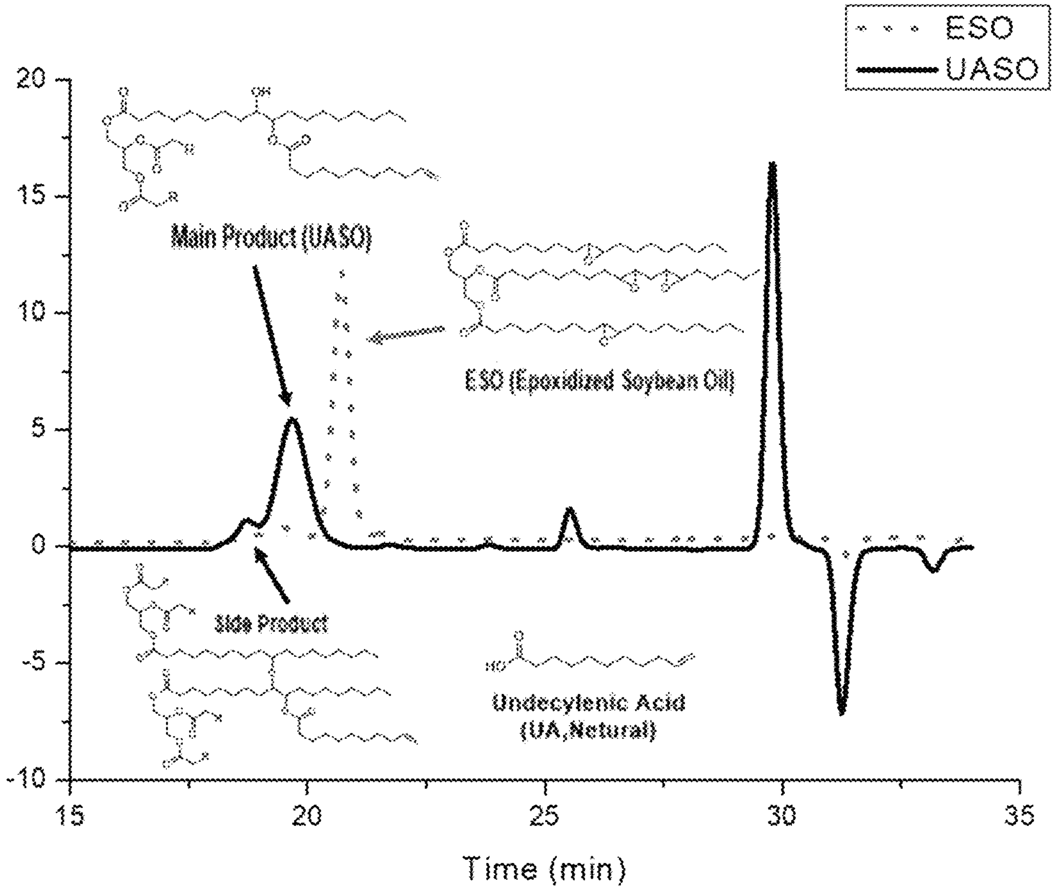

[FIG. 4]
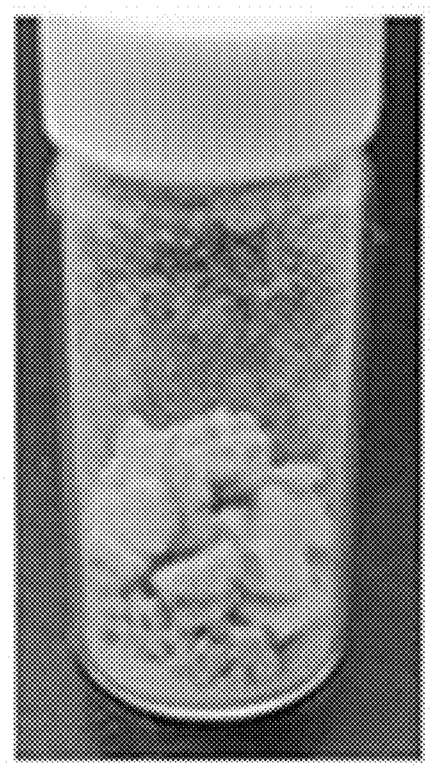

METHOD FOR PREPARING MODIFIED NATURAL OIL USING ORGANOCATALYST SUPPORTED ON POLYMER AND MODIFIED NATURAL OIL PREPARED USING THE SAME

CROSS-REFERENCE TO RELATED APPLICATIONS

This application claims the priority of Korean Patent Application No. 10-2022-0079542 filed on Jun. 29, 2022, in the Korean Intellectual Property Office, the disclosure of which is incorporated herein by reference.

BACKGROUND OF THE INVENTION

Field of the Invention

The present disclosure relates to a method for preparing modified natural oil using an organocatalyst supported on a polymer and a modified natural oil prepared using the same.

Description of the Related Art

Modified natural oils may be used as additives such as plasticizers, compatibilizers or reinforcing agents for various polymers, such as polyvinyl chloride, styrene butadiene rubber, polylactic acid and other polymers (natural rubber, acrylates, etc.). In addition, the modified naturalmoil may serve as a compatibilizer or a secondary plasticizer in blending of polymers. In addition, polyols containing a large amount of hydroxyl groups may be prepared to be also used as a main component of polyurethane.

Such modified natural oil may be prepared through a reaction between natural oil and a nucleophile, but in the related art, it was difficult to recover a catalyst due to the use of a homogeneous organocatalyst for the reaction. Accordingly, in order to reuse such a homogeneous organocatalyst, there is a complicated and inefficient problem that an additional purification process is required. In addition, there is a possibility of denaturation of the homogeneous organocatalyst during the reaction, and there is also a limit in reducing the reuse efficiency.

Considering these points, the present inventors developed a method for preparing modified natural oil using an organocatalyst supported on a polymer.

SUMMARY OF THE INVENTION

An object of the present disclosure is to provide a method for preparing modified natural oil using an organocatalyst supported on a polymer and a modified natural oil prepared using the same.

Another object of the present disclosure is to easily recover and reuse the organocatalyst supported on the polymer used in the preparing method.

Yet another object of the present disclosure is to selectively introduce a functional group by applying an organocatalyst supported on a polymer and various nucleophiles during a ring-opening reaction of epoxidized natural oil in the preparing method.

Still another object of the present disclosure is to improve the production yield of monomers as a main product by adjusting reaction conditions in the method for preparing modified natural oil using the organocatalyst supported on the polymer.

The objects to be solved by the present disclosure are not limited to the aforementioned object(s), and other object(s), which are not mentioned above, will be apparent to those skilled in the art from the following description.

According to an aspect of the present disclosure, the present disclosure provides a method for preparing modified natural oil represented by Chemical Formula 2 below by reacting a nucleophile with epoxidized natural oil represented by Chemical Formula 1 below, wherein an organocatalyst supported on a polymer is used.

[Chemical Formula 1]

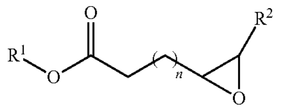

[Chemical Formula 2]

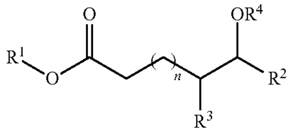

Wherein, $R_1$, $R_2$, $R_3$, and $R_4$ may be the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group may be substituted with substituents selected from hydroxy, amino, alkyl, alkyloxy, alkylamino, dialkylamino, aryl, aryloxy, arylamino, diarylamino, or heteroaryl group, and n may be an integer of 1 to 50.

The nucleophile may be represented by Chemical Formula 3 below.

[Chemical Formula 3]

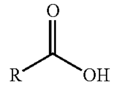

Wherein, R is selected from a substituted or unsubstituted C1 to C10 alkyl group, a substituted or unsubstituted C1 to C10 heteroalkyl group, a substituted or unsubstituted C3 to C10 aryl group, or a substituted or unsubstituted C3 to C10 heteroaryl group.

The nucleophile is an organic acid, and may be one or a combination of two or more selected from caproleic acid, undecylenic acid, myristoleic acid, palmitoleic acid, oleic acid, elaidic acid, gondoic acid, erucic acid, brassic acid, trans-cinnamic acid, benzoic acid, p-anisic acid, and phenylacetic acid.

The content of the nucleophile may be 0.5 to 2 eq. with respect to epoxidized natural oil.

The polymer may be one selected from polystyrene (PS), polyisobutylene (PIB), and polymethyl methacrylate (PMMA).

The organocatalyst supported on the polymer may be tertiary phosphine immobilized to the polymer.

The organocatalyst supported on the polymer may be tertiary amine immobilized to the polymer.

The organocatalyst supported on the polymer may be used in an amount of 20 to 200 mol %.

The reaction, may be performed at 90 to 200° C.

The reaction may be performed for 1 to 48 hours.

The organocatalyst supported on the polymer may be recovered through filtration and reused.

Further, the present disclosure provides a method for preparing modified natural oil comprising (a) preparing modified natural oil represented by Chemical Formula 2 below by reacting a nucleophile and an organocatalyst supported on a polymer with epoxidized natural oil represented by Chemical Formula 1 below; and (b) filtering and separating the organocatalyst supported on the polymer after the reaction of step (a):

[Chemical Formula 1]

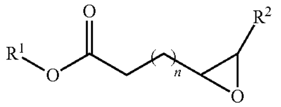

[Chemical Formula 2]

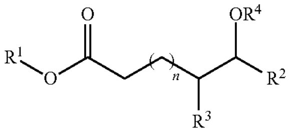

Wherein, $R_1$, $R_2$, $R_3$ and $R_4$ may be the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group may be substituted with substituents selected from hydroxy, amino, alkyl, alkyloxy, alkylamino, dialkylamino, aryl, aryloxy, arylamino, diarylamino, or heteroaryl group, and n may be an integer of 1 to 50.

According to another aspect of the present disclosure, the present disclosure provides modified natural oil represented by Chemical Formula 2 below, which is prepared by the method for preparing the modified natural oil described above:

[Chemical Formula 2]

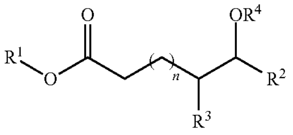

Wherein, $R_1$, $R_2$, $R_3$ and $R_4$ may be the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group may be substituted with substituents selected from hydroxy, amino, alkyl, alkyloxy, alkylamino, dialkylamino, aryl, aryloxy, arylamino, diarylamino, or heteroaryl group, and n may be an integer of 1 to 50.

According to the present disclosure, there is an effect of increasing the content of monomers as the main product of modified natural oil, and minimizing side products.

Further, according to the present disclosure, it is possible to selectively introduce a functional group by applying an organocatalyst supported on a polymer and various nucleophiles.

Further, according to the present disclosure, the organocatalyst supported on the polymer used in the production of modified natural oil can be not only easily recovered and reused repeatedly, but also maintain the efficiency of the reaction because the conversion rate and selectivity of the reaction are not reduced.

It should be understood that the effects of the present disclosure are not limited to the effects, but include all effects that can be deduced from the detailed description of the present disclosure or configurations of the present disclosure described in appended claims.

BRIEF DESCRIPTION OF THE DRAWINGS

FIG. 1 illustrates a process flowchart of a method for preparing modified natural oil using an organocatalyst supported on a polymer according to an embodiment of the present disclosure.

FIG. 2 illustrates results of $^1$H NMR analysis of modified natural, oil prepared using an organocatalyst supported on a polymer, epoxidized soybean oil, and undecylenic acid according to an embodiment of the present disclosure.

FIG. 3 illustrates results of gel permeation chromatography (GPC) analysis of modified natural oil prepared using an organocatalyst supported on a polymer, and epoxidized soybean oil according to an embodiment of the present disclosure.

FIG. 4 is a photograph of an organocatalyst supported on a polymer recovered after production of modified natural oil according to an embodiment of the present disclosure.

DETAILED DESCRIPTION OF THE PREFERRED EMBODIMENT

Before describing the present disclosure in detail, terms or words used in this specification should not be construed as unconditionally limited to a conventional or dictionary meaning, and the inventors of the present disclosure can appropriately define and use the concept of various terms in order to describe their invention in the best method. Furthermore, it should be understood that these terms or words should be interpreted as meanings and concepts consistent with the technical idea of the present disclosure.

That is, the terms used in the present disclosure are only used to describe a preferred embodiment of the present disclosure, and are not intended to specifically limit the contents of the present disclosure, and it should be noted that these terms are terms defined in consideration with various possibilities of the present disclosure.

In addition, in this specification, it should be understood that the singular expression may include a plural expression: unless clearly indicated in another meaning in the context, and even if similarly expressed in the plural, the singular expression may include the meaning of the singular number.

Throughout the present disclosure, when a component is described as "including" the other component, the component does not exclude any other component, but may further include any other component unless otherwise indicated in contrary.

Further, hereinafter, in the following description of the present disclosure, a detailed description of a configuration determined to unnecessarily obscure the subject matter of the present disclosure, for example, known technologies including the related arts may be omitted.

Hereinafter, the present disclosure will be described in more detail.

Method for Preparing Modified Natural Oil

The present disclosure provides a method for preparing modified natural oil represented by Chemical Formula 2 below by reacting a nucleophile with epoxidized natural oil represented by Chemical Formula 1 below, wherein an organocatalyst supported on a polymer is used.

FIG. 1 is a process flowchart of a method for preparing modified natural oil of the present disclosure.

Referring. FIG. 1, the method for preparing modified natural oil of the present disclosure includes preparing modified natural oil by reacting epoxidized natural oil with a nucleophile and an organocatalyst supported on a polymer (S10); and filtering and separating the organocatalyst supported on the polymer (S20).

Hereinafter, the method will be described in detail for each step.

(a) preparing modified natural oil represented by Chemical Formula 2 below by reacting epoxidized natural oil represented by Chemical Formula 1 below with a nucleophile and an organocatalyst supported on a polymer (S10).

[Chemical Formula 1]

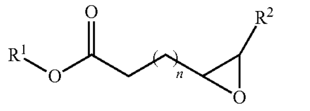

[Chemical Formula 2]

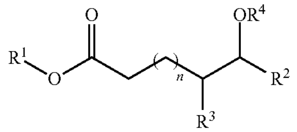

Wherein, $R_1$, $R_2$, $R_3$ and $R_4$ are the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group are substituted with substituents selected from hydroxy, amino, alkyl, alkyloxy, alkylamino, dialkylamino, aryl, aryloxy, arylamino, diarylamino, or heteroaryl group, and n is an integer of 1 to 50.

The reaction in step S10 may be represented by Reaction Formula 1 below.

[Reaction Formula 1]

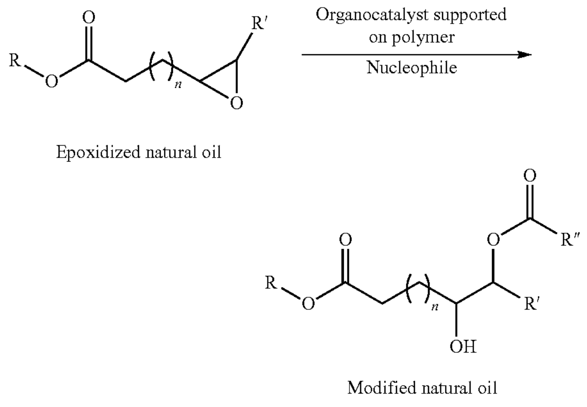

The epoxidized natural oil represented by Chemical Formula 1 (the left side of Reaction Formula 1) may be preferably epoxidized soybean oil (ESO or ESBO), but is not limited thereto. The epoxidized soybean oil is a non-toxic, clear yellow liquid used as a plasticizer or stabilizer in PVC and its copolymers.

The monomer of the epoxidized soybean oil contains an average of 4 epoxy functional groups (oxirane ring).

The organocatalyst supported on the polymer refers to an organocatalyst immobilized on the polymer and may be represented as shown in the following diagram.

[Organocatalyst Supported on Polymer]

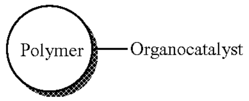

The polymer used in the organocatalyst supported on the polymer may be one selected from polystyrene (PS), polyisobutylene (PIB), and polymethyl methacrylate (PMMA), but is not limited thereto.

The organocatalyst used for the organocatalyst supported on the polymer may be phosphine-based or amine-based.

The organocatalyst supported on the polymer may be an organocatalyst in which phosphine is immobilized to the polymer. In addition, it is preferable that tertiary phosphine is immobilized to the polymer, and the tertiary phosphine immobilized to the polymer may be represented by [polymer-$PR_1R_2R_3$]. Wherein, the polymer is linked to an R group ($R_1$, $R_2$ or $R_3$) of the tertiary phosphine or the polymer is linked instead of the R group as represented in Table A below. In the Table A below, the polymer is represented by a circle (or sphere).

TABLE A

| |
|---|
| 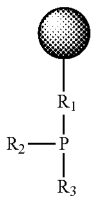 |
| 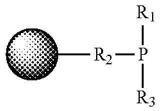 |
| 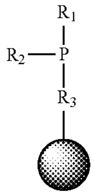 |
| 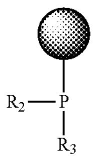 |
| 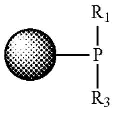 |

TABLE A-continued

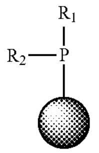

The $R_1$, $R_2$, and $R_3$ are the same or different, and may be selected from a substituted or unsubstituted C1 to C10 alkyl group, a substituted or unsubstituted C1 to C10 heteroalkyl group, a substituted or unsubstituted C3 to C10 aryl group, and a substituted or unsubstituted C3 to C10 heteroaryl group.

As an example of the phosphine-based organocatalyst supported on the polymer, triphenylphosphonium (TPP) may be used.

The organocatalyst supported on the polymer may be an organocatalyst in which amine is immobilized to the polymer. In addition, it is preferable that tertiary amine is immobilized to the polymer, and the tertiary amine immobilized to the polymer may be represented by [polymer-$NR_1'R_2'R_3'$]. Wherein, the polymer is linked to an R group ($R_1'$, $R_2'$ or $R_3'$) of the tertiary amine or the polymer is linked instead of the R group as represented in Table B below. In the Table B below, the polymer is represented by a circle (or sphere).

TABLE B

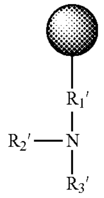

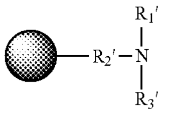

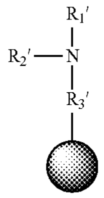

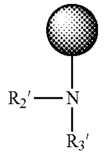

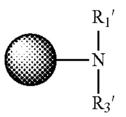

TABLE B-continued

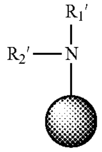

The $R_1'$, $R_2'$, and $R_3'$ are the same or different, and may be selected from a substituted or unsubstituted C1 to C10 alkyl group, a substituted or unsubstituted C1 to C10 heteroalkyl group, a substituted or unsubstituted C3 to C10 aryl group, and a substituted or unsubstituted C3 to C10 heteroaryl group. As an example of the amine-based organocatalyst supported on the polymer, dimethylaminopyridine (DMAP) or piperidine may be used.

Examples of the organocatalyst supported on the polymer according to an embodiment of the present disclosure include DMAP, piperidine, TPP, and the like supported on the polymer as shown in the Table C below. In the Table C below, the polymer is represented by a circle (or sphere).

TABLE C

| | |
|---|---|
| DMAP catalyst supported on polymer | 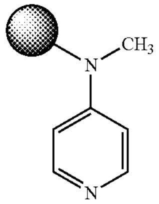 |
| Piperidine catalyst supported on polymer | 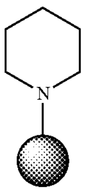 |
| TPP catalyst supported on polymer | 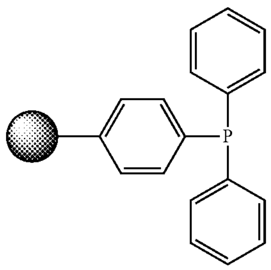 [SMILES: Cc1ccc(P(c2ccccc2)c2ccccc2)cc1] |

The nucleophile may be represented by Chemical Formula 3 below.

[Chemical Formula 3]

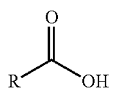

Wherein, R is selected from a substituted or unsubstituted C1 to C10 alkyl group, a substituted or unsubstituted C1 to C10 heteroalkyl group, a substituted or unsubstituted C3 to C10 aryl group, and a substituted or unsubstituted C3 to C10 heteroaryl group.

The nucleophile is an organic acid, and may be at least one selected from caproleic acid, undecylenic acid, myristoleic acid, palmitoleic acid, oleic acid, elaidic acid, gondoic acid, erucic acid, brassic acid, trans-cinnamic acid, benzoic acid, p-anisic acid, and phenylacetic acid.

The content of the nucleophile may be 0.5 to 2 eq., more preferably 0.75 to 1.5 eq., with respect to epoxidized natural oil. It is preferred that one nucleophile molecule react with one epoxy functional group. Since epoxidized soybean oil monomers contain an average of 4 oxirane rings, 1 eq. of the nucleophile may be calculated as [mmol of epoxidized natural oil×4 (the number of epoxy rings in ESO)].

The organocatalyst supported on the polymer may be used in an amount of 20 to 200 mol % (0.2 to 2 eq.), more preferably 50 to 150 mol % (0.5 to 1.5 eq.) with respect to oxirane rings (epoxy groups) in epoxidized natural oil.

The conversion rate to the modified natural oil prepared according to the preparation method of the present disclosure may be 80% or more, preferably 80% to 99% based on a starting material (Table 1).

In addition, in relation to the selectivity to the modified natural oil prepared according to the preparation method of the present disclosure, the content of the monomers as the main product may be 65% or more, preferably 80 to 95% with respect to the total modified natural oil. Referring to Table 1, it can be seen that when the nucleophile is 1 to 1.5 eq. (1 eq. of nucleophile=mmol of ESO×4) and the catalyst content is 0.5 to 1.5 eq. (1 eq. of catalyst=mmol of ESO×4=100 mol %), the monomers as the main product are produced at 80% or more and 95% or less in the total modified natural oil.

An example of a monomer as the main product to be produced in the present disclosure and a dimer as an example of a side product are shown below.

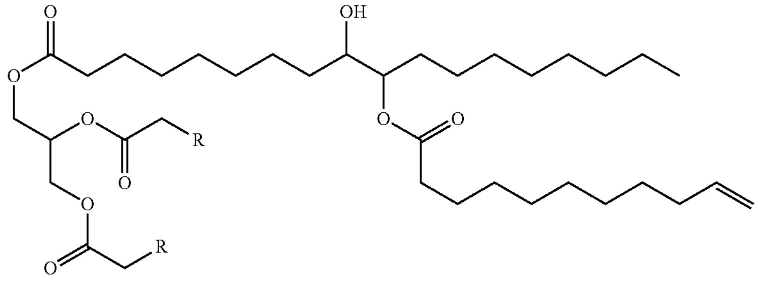

[Main product]

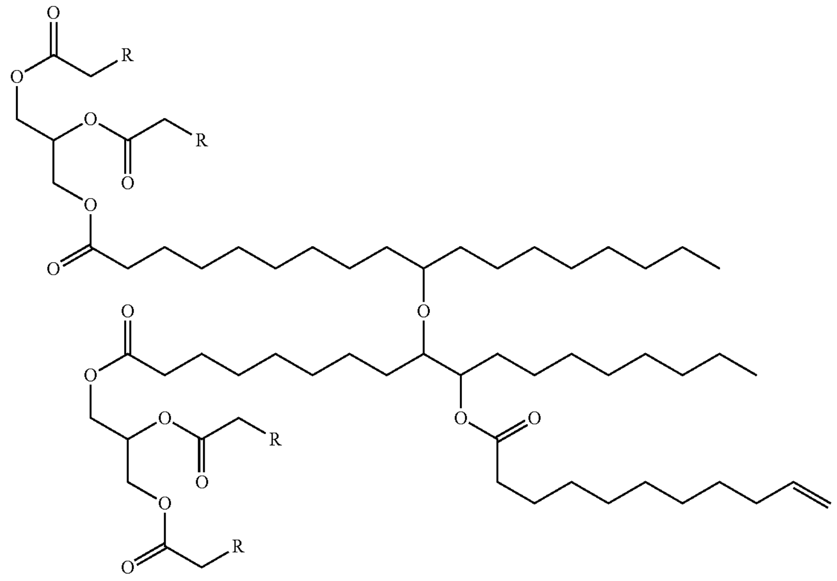

[Side product]

The reaction may be performed at 90 to 200° C., preferably at 120 to 180° C., and more preferably at 130 to 170° C.

The reaction may be performed for 1 to 50 hours, preferably for 3 to 48 hours.

The conversion rate and selectivity to the modified natural oil prepared according to the preparation method of the present disclosure are excellent, and the conversion rate and selectivity may be improved by adjusting the reaction conditions.

(b) filtering and separating the organocatalyst supported on the polymer after the reaction in step (a) (S20).

In step (S20), the organocatalyst supported on the polymer used in the reaction in step (a) may be recovered by filtering through a filter and reused. Preferably, the organocatalyst supported on the polymer recovered by filtration may be washed and dried and then reused for the reaction in step (a).

Referring to Table 2, it can be seen that there is no change in conversion rate and selectivity even when the organocatalyst supported on the polymer is repeatedly reused.

Modified Natural Oil

The present disclosure provides modified natural oil represented by Chemical Formula 2 below, which is prepared by the method for preparing the modified natural oil described above:

[Chemical Formula 2]

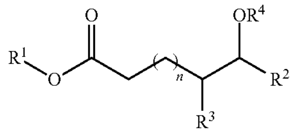

Wherein, $R_1$, $R_2$, $R_3$ and $R_4$ are the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group are substituted with substituents selected from hydroxy, amino, alkyl, alkyloxy, alkylamino, dialkylamino, aryl, aryloxy, arylamino, diarylamino, or heteroaryl group, and n is an integer of 1 to 50.

The monomer content of the modified natural oil may be 50% to 95%, preferably 65% to 95%, and more preferably 80% to 95% of the total modified natural oil.

Example

Hereinafter, the present disclosure will be described in detail with reference to Examples for specific description. However, Examples according to the present disclosure may be modified in various forms, and it is not interpreted that the scope of the present disclosure is limited to the following Examples. Examples of the present disclosure will be provided for more completely explaining the present disclosure to those skilled in the art.

<Materials>

Epoxidized soybean oil (ESO) was purchased from Sajo, and undecylenic acid or trans-cinnamic acid was used as an organic acid, which was purchased from Sigma Aldrich. Chemical Formulas of the epoxidized soybean oil, the organic acids and catalysts supported on the polymer used in Example were as follows.

[Epoxidized soybean oil]

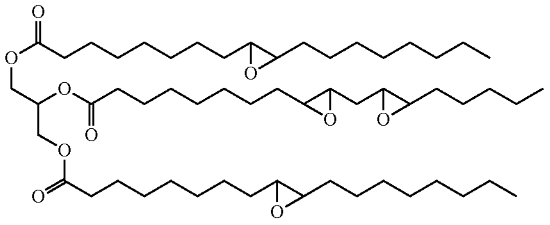

ESO (Epoxidized Soybean Oil)

[Undecylenic acid]

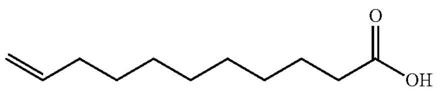

Undecylenic Acid
(UA, Natural)

-continued

[Trans-cinnamic acid]

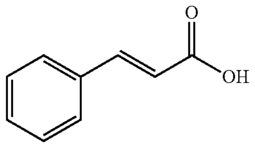

trans-Cinnamic Acid
(CA, Natural)

[DMAP catalyst supported on polymer]

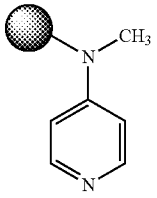

[Piperidine catalyst supported on polymer]

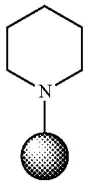

[TPP catalyst supported on polymer]

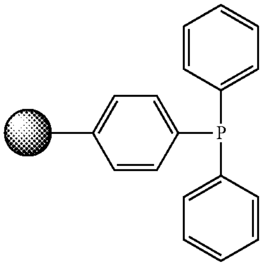

Example 1

Reaction Formula of Example 1 was as follows.

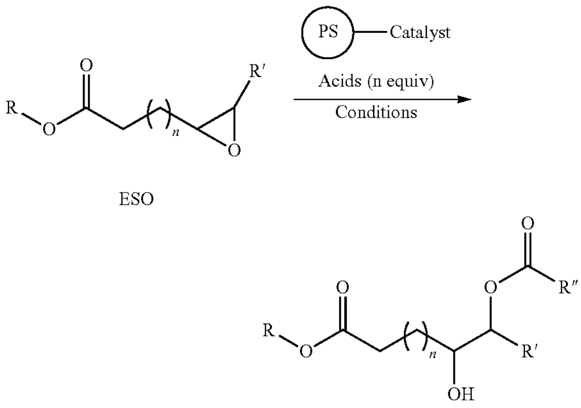

Example 1-1 was performed as follows. In a 20 mL vial, a stirring bar, epoxidized soybean oil (ESO, 1.0 mL, 1.05 mmol), a DMAP catalyst supported on polystyrene (PS-DMAP, 1 eq.=100 mol %) and undecylenic acid (1 eq.=4.20 mmol, 0.774 g) were added.

Then, the vial was placed in an oil bath heated to 130° C. and the reaction proceeded for 24 hours. After the reaction was completed, the vial was cooled to room temperature, and then the vial was opened and a sample was taken. For this sample, the conversion rate was analyzed through $^1H$ NMR and the selectivity of the main product/side product of modified natural oil was analyzed through GPC, as illustrated in FIGS. 2 and 3.

The nucleophiles, the catalysts, the solvents, and the reaction conditions of Examples 1-2 to 1-10 were shown in Table 1 below, and except for these, the reactions were performed in the same manner as in Example 1-1.

TABLE 1

| Examples[a] | Nucleophile (eq.) | Catalyst (mol %) | Solvent | Temperature (° C.)/time(h) | Conversion rate(%)[b] | Number average molecular weight[c] (monomer:dimer) |
|---|---|---|---|---|---|---|
| 1-1 | UA (1.0) | PS-DMAP (100) | — | 130/24 | 80 | 1484:3112 (85:15) |
| 1-2 | UA (1.0) | PS-DMAP (50) | — | 130/24 | 84 | 1513:3130 (95:5) |
| 1-3 | UA (1.0) | PS-Piperidine (50) | — | 130/24 | 98 | 1550:3171 (83:17) |
| 1-4 | UA (1.0) | PS-Piperidine (100) | — | 130/24 | 98 | 1480:3047 (84:16) |
| 1-5[d] | UA (1.0) | PS-Piperidine (100) | — | 130/24 | 91 | 1651:4909 (88:12) |
| 1-6[d] | UA (1.0) | PS-Piperidine (100) | Ethyl acetate | 130/24 | 65 | 1829:4613 (90:10) |
| 1-7[d] | UA (1.5) | PS-Piperidine (100) | — | 130/24 | 91 | 1980:4889 (86:14) |
| 1-8[d] | UA (1.0) | PS-Piperidine (150) | — | 130/24 | 90 | 1954:5123 (88:12) |
| 1-9[d] | UA (1.0) | PS-Piperidine (100) | — | 130/48 | 94 | 1989:5113 (87:13) |
| 1-10 | CA (0.75) | PS-TPP (50) | — | 170/3 | 99 | 1154:2699 (67:33) |

[a]Reaction conditions: ESO (1.05 mmol, 1 mL), nucleophile (1.05 [mmol of ESO] x 4 [number of epoxy rings in ESO] x equivalent number)
[b]Conversion rate based on $^1H$ NMR of oxirane rings in ESO (initial ESO − residual ESO)
[c]Number average molecular weight ($M_n$) based on GPC (Standard: PS)
[d]performed under pressure conditions
* ESO = Epoxidied Soybean Oil, DMAP = 4-(DiMethylAmino)Pyridine, TPP = TriPhenylPhosphine FIG. 2 is a comparative analysis of $^1H$ NMR of undecylenic acid esterified soybean oil (UASO) produced in Example 1 with 1H NMR of epoxidized soybean oil (ESO) and undecylenic acid (UA). Through this, the conversion rate may be calculated by comparing the number of epoxy rings per molecule of a starting material ESO before the reaction with the number of epoxy rings remaining after the reaction, and as a result, the conversion rates were shown in Table 1.

FIG. 3 illustrates GPC analysis results of UASO, which was the main product according to Example 1, compared with the GPC analysis results of ESO. As a result, it can be seen that the selectivity may be calculated by calculating an area ratio between a peak of the main product UASO and a peak of the side product, and according to the present disclosure, the ratio of the main product UASO may be increased.

Referring to Table 1, when the nucleophile content was 0.75 eq. or more and 1.5 eq. or less with respect to the epoxidized soybean oil, the content of the main product of modified natural oil was produced to 65% or more and 95% or less. In addition, when the nucleophile content was 1 eq. or more and 1.5 eq. or less with respect to the epoxidized soybean oil, the content of the main product of modified natural oil was produced to 80% or more and 95% or less.

Example 2

Reaction Formula of Example 2 was as follows.

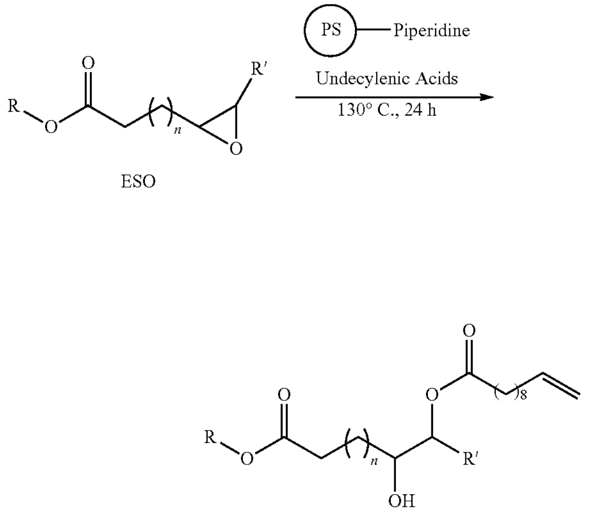

ESO

After the reaction of Example 1-5 was performed using a 15 mL pressure vessel, the used organocatalyst supported on the polymer was filtered through filtration. The catalyst which was washed with ethyl acetate (10 mL×3) and then recovered on the filter was dried using an oven, and then the reaction of Example 1 was performed again to confirm reusability. The process was repeated up to 3 cycles, and the results were shown in Table 2 and FIG. 4.

TABLE 2

| Number of reuses [a] | Conversion rate [b] | Selectivity [c] |
|---|---|---|
| 1 | 91 | 88 |
| 2 | 95 | 88 |
| 3 | 97 | 88 |

[a] Reaction conditions: ESO (1.05 mmol, 1 mL), undecylenic acid & PS-piperidine (1.05 [mmol of ESO] × 4[number of epoxy rings of ESO] × 1 eq., 4.2 mmol), 130° C., 24 hours, catalyst washed twice with ethyl acetate before recycle test

[b] Conversion rate based on $^1$H NMR of oxirane rings in ESO ([initial − residual ESO epoxy groups/initial epoxy group]*100)

[c] Selectivity based on ratio of main product and side product of number average molecular weight (Mn) using GPC (standard: PS, [main product/total]*100)

FIG. 4 is a photograph of powder obtained by drying the catalyst (PS-piperidine) recovered in Example 2.

Referring to Table 2, it was found that the conversion rate and selectivity were not lowered even when the organocatalyst supported on the polymer according to the present disclosure was repeatedly reused.

So far, the specific embodiments of the method for preparing the modified natural oil using the organocatalyst supported on the polymer according to an embodiment of the present disclosure and the modified natural oil produced using the same have been described, but it is obvious that various implementation modifications are made without departing from the scope of the present disclosure.

Therefore, the scope of the present disclosure should not be limited to the exemplary embodiments and should be defined by the appended claims and equivalents to the appended claims.

In other words, the exemplary embodiments described above are illustrative in all aspects and should be understood as not being restrictive, and the scope of the present disclosure is represented by appended claims to be described below rather than the detailed description, and it is to be interpreted that the meaning and scope of the appended claims, and all changed or modified forms derived from the equivalents thereof are included within the scope of the present disclosure.

What is claimed is:

1. A method for preparing modified natural oil represented by Chemical Formula 2 below by reacting a nucleophile with epoxidized natural oil represented by Chemical Formula 1 below, wherein an organocatalyst supported on a polymer is used:

[Chemical Formula 1]

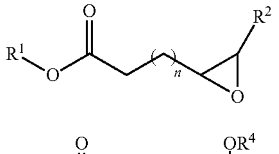

[Chemical Formula 2]

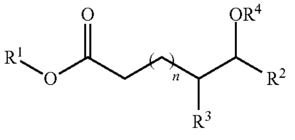

Wherein, $R_1$, $R_2$, $R_3$ and $R_4$ are the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group are substituted with substituents selected from hydroxy, amino, alkyl, alkyloxy, alkylamino, dialkylamino, aryl, aryloxy, arylamino, diarylamino, or heteroaryl group, and n is an integer of 1 to 50, wherein the content of the nucleophile is 1 to 2 eq. with respect to epoxidized natural oil, wherein the organocatalyst supported on the polymer is a tertiary phosphine or a tertiary amine immobilized to the polymer, and wherein the organocatalyst supported on the polymer is used in an amount of 50 to 150 mol % with respect to oxirane rings in epoxidized natural oil.

2. The method for preparing modified natural oil of claim 1, wherein the nucleophile is represented by Chemical Formula 3 below:

[Chemical Formula 3]

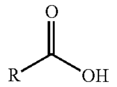

Wherein, R is selected from a substituted or unsubstituted C1 to C10 alkyl group, a substituted or unsubstituted C1 to C10 heteroalkyl group, a substituted or unsubstituted C3 to C10 aryl group, or a substituted or unsubstituted C3 to C10 heteroaryl group.

3. The method for preparing modified natural oil of claim 1, wherein the nucleophile is an organic acid, and is one or a combination of two or more selected from caproleic acid, undecylenic acid, myristoleic acid, palmitoleic acid, oleic acid, elaidic acid, gondoic acid, erucic acid, brassic acid, trans-cinnamic acid, benzoic acid, p-anisic acid, and phenylacetic acid.

4. The method for preparing modified natural oil of claim 1, wherein the polymer is one selected from polystyrene (PS), polyisobutylene (PIB), and polymethyl methacrylate (PMMA).

5. The method for preparing modified natural oil of claim 1, wherein the reaction is performed at 90 to 200° C.

6. The method for preparing modified natural oil of claim 1, wherein the reaction is performed for 1 to 48 hours.

7. The method for preparing modified natural oil of claim 1, wherein the organocatalyst supported on the polymer is recovered through filtration and reused.

8. A method for producing modified natural oil comprising:

(a) preparing modified natural oil represented by Chemical Formula 2 below by reacting a nucleophile and an organocatalyst supported on a polymer with epoxidized natural oil represented by Chemical Formula 1 below, wherein the content of the nucleophile is 1 to 2 eq. with respect to epoxidized natural oil, wherein the organocatalyst supported on the polymer is a tertiary phosphine or a tertiary amine immobilized to the polymer, and wherein the organocatalyst supported on the polymer is used in an amount of 50 to 150 mol % with respect to oxirane rings in epoxidized natural oil; and (b) filtering and separating the organocatalyst supported on the polymer after the reaction of step (a):

[Chemical Formula 1]

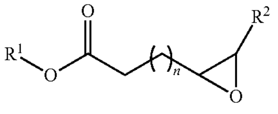

-continued

{Chemical Formula 2]

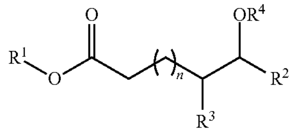

wherein, $R_1$, $R_2$, $R_3$ and $R_4$ are the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group are substituted with substituents selected from hydroxy, amino, alkyl, alkyloxy, alkylamino, dialkylamino, aryl, aryloxy, arylamino, diarylamino, or heteroaryl group, and n is an integer of 1 to 50.

9. Modified natural oil represented by Chemical Formula 2 below:

[Chemical Formula 2]

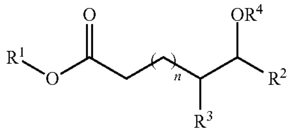

wherein, $R_1$, $R_2$, $R_3$ and $R_4$ are the same or different, and substitutable hydrocarbon groups, and represent an alkyl group having 1 to 10 carbon atoms, or an aryl group or heteroaryl group having 3 to 10 ring atoms, and the alkyl group, the aryl group, and the heteroaryl group are substituted with substituents selected from hydroxy, amino, alkyl, alkyloxy, alkylamino, dialkylamino, aryl, aryloxy, arylamino, diarylamino, or heteroaryl group, and n is an integer of 1 to 50, wherein, in a GPC chromatogram of the modified natural oil, a peak area of the monomer is 80% to 95% based on a combined peak area of the monomer and side products.

* * * * *